United States Patent [19]
Yoshida

[11] Patent Number: 5,619,325
[45] Date of Patent: Apr. 8, 1997

[54] OPTICAL SYSTEM FOR ELLIPSOMETRY UTILIZING A CIRCULARLY POLARIZED PROBE BEAM

[75] Inventor: Haruo Yoshida, Saitama, Japan

[73] Assignee: Advantest Corporation, Tokyo, Japan

[21] Appl. No.: 628,964

[22] Filed: Apr. 4, 1996

[30] Foreign Application Priority Data

| Apr. 4, 1995 | [JP] | Japan | 7-102958 |
| Apr. 19, 1995 | [JP] | Japan | 7-117809 |
| May 23, 1995 | [JP] | Japan | 7-148330 |

[51] Int. Cl.⁶ .................................................. G01B 9/02
[52] U.S. Cl. ...................................... 356/351; 356/349
[58] Field of Search ................................ 356/345, 349, 356/351

[56] References Cited

U.S. PATENT DOCUMENTS

| 4,842,408 | 6/1989 | Yoshii et al. | 356/351 |
| 5,526,118 | 6/1996 | Miyagawa et al. | 356/349 |
| 5,528,369 | 6/1996 | Starkey | 356/351 |

FOREIGN PATENT DOCUMENTS

| 2227830 | 8/1990 | European Pat. Off. | 356/351 |

Primary Examiner—Frank Gonzalez
Assistant Examiner—Robert Kim
Attorney, Agent, or Firm—Knobbe, Martens, Olson & Bear, LLP

[57] ABSTRACT

An ellipsometry optical system is to analyze light beams reflected from or transmitted through optical devices or materials. The ellipsometry optical system includes a light source for generating a coherent light beam; a first beam splitter for splitting the coherent light beam into two light beams; an optical frequency shifter for shifting a frequency of one of the two light beams splitted by the first beam splitter to form a reference light beam; a circular polarization converter for circularly polarizing the other of the two light beams splitted by the first beam splitter to form a probing light beam which is a circularly polarized light beam to be applied to the optical device under test; a second beam splitter for combining the reference light beam and the probing light beam that transmitted through the optical device under test; a birefringence prism for receiving a light beam combined by the second beam splitter and separating polarization components which are perpendicular with each other; and a photo detector for receiving the polarization components and converting the same to corresponding electric signals.

21 Claims, 5 Drawing Sheets

OPTICAL SYSTEM FOR ELLIPSOMETRY UTILIZING A CIRCULARLY POLARIZED PROBE BEAM

FIELD OF THE INVENTION

This invention relates to an optical system for ellipsometry to analyze light beams reflected from or transmitted through optical devices or materials, and more particularly, to an ellipsometry optical system including a polarization dependent loss measurement system to accurately measure the loss in the transmitted or reflected light beams which is dependent on the polarization characteristics of the optical devices or materials at high speed and high sensitivity.

BACKGROUND OF THE INVENTION

Most of the optical materials such as optical fibers, optical connectors or other optical components are subject to a birefringence when an optical path for an incident light beam is deviated from optical axes of the materials. Namely, an optical beam is polarized when passing through or reflected from such birefringent materials. Thus, for example, when a circularly polarized light beam is emitted to a birefringent material and is transmitted through the birefringent material or reflected by the birefringent material, the circular polarization of the light beam is affected to be an elliptically polarized or linearly polarized light beam. As a result of such birefringence, the light beam suffers a loss of power, i.e., subject to the polarization dependent loss.

Figure 7A:
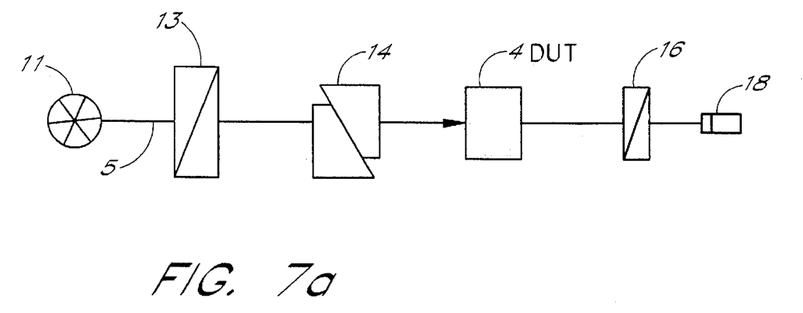
FIG. 7A is a block diagram showing a conventional measuring method using a Soleil-Babinet compensator.
Figure 7B:
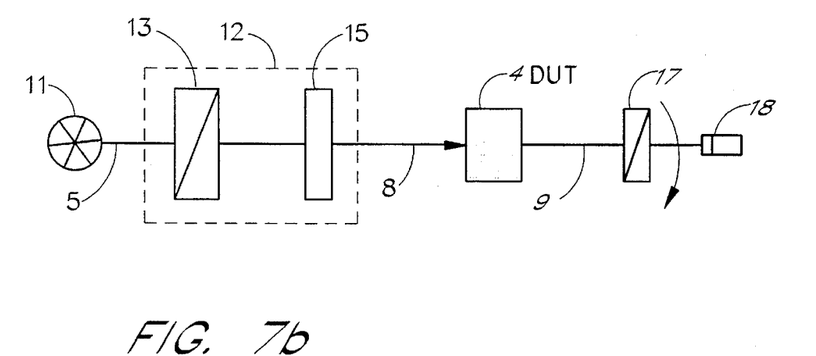
FIG. 7B is a block diagram showing a conventional measuring method using a rotating analyzer.
Figure 7C:
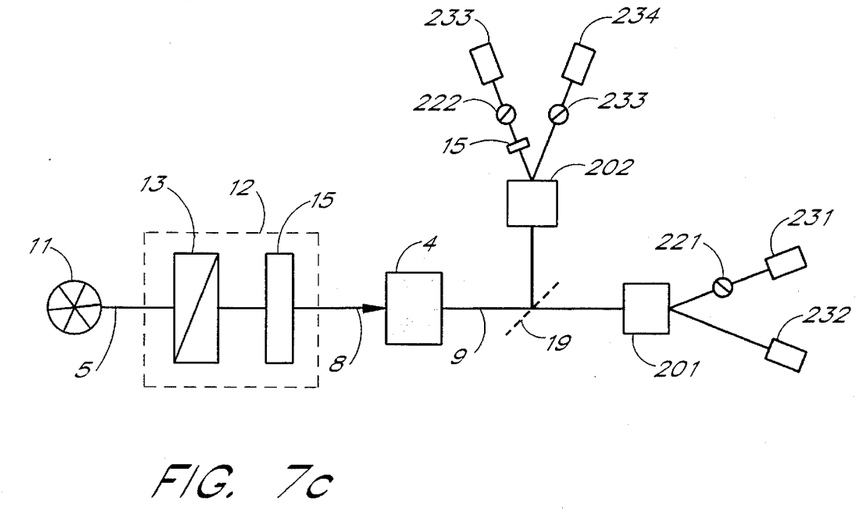
FIG. 7C is a block diagram showing a conventional measuring method based on an amplitude splitting process.

To determine the polarization characteristics or the amount of the polarization dependent loss of the optical material by measuring an azimuth (polarization angle) and an ellipticity, the conventional technologies shown in FIG. 7 have been generally used. FIG. 7A is a block diagram showing a conventional measuring method using a Soleil-Babinet compensator 14, FIG. 7B is a block diagram showing a conventional measuring method using a rotating analyzer 17, and FIG. 7C is a block diagram showing a conventional measuring method based on a power splitting process.

In FIG. 7A, a light source 11 emits a coherent light beam 5 which passes through a polarizer 13, a Soleil-Babinet compensator 14, and a device under test (DUT) 4. The DUT 4 in this case is a type of optical material or device through which the light beam 5 can transmit. The light beam from the DUT 4 is received by an analyzer 16 and a photo detector 18.

The polarizer 13 is to separate a certain polarization in the light beam from the other. The analyzer 16 has the same structure of polarizer 13 and is used for detecting the polarization of the incoming light beam. The Soleil-Babinet compensator 14 is to adjust the degree of birefringence in the light beam passing therethrough by changing a mechanical position of wedges forming the compensator. The photo detector 18 is typically a photo diode to detect the optical signal and converts the detected optical signal to a corresponding electric signal.

In the arrangement of FIG. 7A, prior to the measurement of the light beam from the DUT 4, the polarizer 13 and the analyzer 16 are first adjusted without the DUT 4 and the Soleil-Babinet compensator 14. The adjustment is made so that the optical axes of the polarizer 13 and the analyzer 16 are perpendicular with each other. In this situation, when the coherent light beam 5 is emitted, the light beam 5 is prohibited to reach the photo detector 18 because of the optical axes. Thus, the output electric current produced by the photo detector 18 is the smallest amount. When inserting the DUT 4 between the polarizer 13 and the analyzer 16 as shown in FIG. 7A, a small amount of light beam passes through the analyzer 16 and reaches the photo detector 18 since the light beam 5 is elliptically polarized by the DUT 4.

Then the Soleil-Babinet compensator 14 is inserted between the polarizer 13 and the DUT 4, and the wedge of the compensator 14 is adjusted by, for example, a micrometer head (not shown), until a point will be found where the light beam is again prohibited to reach the photo detector 18. In this point, the output electric current of the photo detector 18 becomes the minimum amount as above.

In this situation, the azimuth and ellipticity of the polarization caused by the DUT 4 can be calculated base on the reading of the micrometer which has driven the Soleil-Babinet compensator 14. Further, based on the azimuth and ellipticity thus obtained, a polarization dependent loss can also be calculated. In the example of foregoing process, the minimum point of input power to the photo detector 18 is detected. In a similar manner, it is also possible to utilize the maximum point of power as a target point by arranging the polarizer 13 and the analyzer 16 in the same optical axis.

In the example of FIG. 7B, a light source 11 provides a coherent light beam 5 which passes through a circular polarization converter 12, and a device under test (DUT) 4. The light beam from the DUT 4 is received by a rotating analyzer 17 and a photo detector 18.

The circular polarization converter 12 is formed of a polarizer 13 and a ¼ wavelength ($\lambda/4$) plate 15. The circular polarization converter 12 is to convert an incoming light beam 5 to a circularly polarized light beam 8. The rotating analyzer 17 is basically the same as the analyzer 16 of FIG. 7A, however it mechanically rotates by a predetermined constant rotation rate. The photo detector 18 is typically a photo diode to detect the optical signal and converts the detected optical signal to a corresponding electric signal.

The light beam 5 emitted from the light source 11 is converted to a circularly polarized light beam 8 by the circular polarization converter 12. The DUT 4 is irradiated by the circularly polarized light beam 8 and the resulted light beam 9 from the DUT 4 may be elliptically polarized because of the birefringence of the DUT 4. The transmitted light beam 9 reaches the photo detector 18 through the rotating analyzer 17.

Since the rotating analyzer 17 rotates in the constant rate, the light beam detected by the photo detector 18 periodically changes its intensity. In other words, the light beam passing through the rotating analyzer 17 is converted to an alternating signal having the high intensity light beam and the low intensity light beam. This is because the light beam is intensified when the optical axes of the DUT 4 and the rotating analyzer 17 are aligned while the light beam is weakened when the optical axes of the DUT 4 and the rotating analyzer 17 intersect at 90 degrees. Thus, the azimuth and ellipticity caused by the DUT 4 can be calculated based on the rotation angle of the rotating analyzer 17. Further, based on the azimuth and ellipticity thus obtained, a polarization dependent loss can also be calculated.

In the example of FIG. 7C, like the example of FIG. 7B, a light source 11 provides a coherent light beam 5 which passes through a circular polarization converter 12, and a device under test (DUT) 4. Unlike the example of FIG. 7B, the light beam from the DUT 4 is received by a beam splitter 19, Wollaston prisms 201 and 202, polarization plates 221, 222 and 223, a $\lambda/4$ plate 152, and photo detectors 231–234 as shown in FIG. 7C.

The circular polarization converter 12 is formed of a polarizer 13 and a λ/4 plate 15₁. The circular polarization converter 12 is to convert an incoming input light beam 5 to a circularly polarized light beam 8. The beam splitter 19 splits the circularly polarized light beam 8 into two light beams, one goes straight forward and the other goes upper direction in FIG. 7C. The Wollaston prisms 201 and 202 are birefringent polarization prisms which separate the light beam passing therethrough into an ordinary beam and an extraordinary beam. The optical axes of the ordinary beam and the extraordinary beam from the Wollaston prism are perpendicular with each other.

Thus, by properly aligning the optical axes of the Wollaston prisms 201 and 202, and by passing through the λ/4 plate 152 and the polarization plates 221–223, each of the four polarization components can be detected by the corresponding photo detectors 231–234. By comparing the intensities of the four polarization components detected by the photo detectors 231–234, the polarization state such as the azimuth and ellipticity caused by the DUT 4 can be calculated. Further, based on the azimuth and ellipticity thus obtained, a polarization dependent loss of the DUT 4 can also be calculated.

In the foregoing conventional measuring methods, for example in FIG. 7A using the Soleil-Babinet compensator or in FIG. 7B using the rotating analyzer, a relatively large response time is required since these methods involve the mechanically moving parts. Thus, in the examples of FIGS. 7A and 7B, it is not possible to realize a high speed measurement. In the example of FIG. 7C, a detection sensitivity is low, since the light signal from the device under test is divided into four light beams. Thus, it is difficult to improve the measurement accuracy or sensitivity in the example of FIG. 7C.

SUMMARY OF THE INVENTION

Therefore, it is an object of the present invention to provide an optical system for ellipsometry which is capable of analyzing light beams reflected from or transmitted through optical devices under test and of determining a polarization dependent loss caused by the optical devices under test without problems associated in the conventional technology.

It is another object of the present invention to provide an optical system for ellipsometry which is capable of analyzing light beams reflected from or transmitted through optical devices under test without including mechanically moving components.

It is a further object of the present invention to provide an optical system for ellipsometry which is capable of analyzing light beams reflected from or transmitted through optical devices under test at high speed.

It is a further object of the present invention to provide an optical system for ellipsometry which is capable of analyzing light beams reflected from or transmitted through optical devices under test at high detection sensitivity.

It is a further object of the present invention to provide an optical system for ellipsometry which is capable of analyzing light beams reflected from or transmitted through optical devices under test based on a heterodyne discrimination technology including frequency shifters.

It is a further object of the present invention to provide an optical system for ellipsometry which is capable of analyzing light beams reflected from or transmitted through optical devices under test at high accuracy by handling relatively low frequency electric signals in a signal analysis process.

It is a further object of the present invention to provide an optical system for ellipsometry which is capable of analyzing light beams reflected from or transmitted through optical devices under test with high resolution by using band pass filters for each polarization component to reduce noises occurred in the optical system.

In the present invention, the optical system for ellipsometry is to analyze light beams reflected from or transmitted through optical devices or materials (DUT). The ellipsometry optical system of the present invention measures a polarization dependent loss in the transmitted or reflected light beams from the optical devices or materials at high speed and high sensitivity.

The ellipsometry optical system of the present invention employs a heterodyne principle to beat down a frequency of a light beam which has been elliptically polarized by transmitting through the DUT. The heterodyne process is undertaken by mixing the light beam passing through the DUT with a reference light which is frequency shifted by several MHz–100 MHz. The Composite light signal has a frequency which is equal to the frequency shift and includes information on the polarization state of the light beam that has passed through the DUT. The composite light beam is provided to a birefringent polarization prism whereby it is divided into two polarization components which are orthogonal with each other.

These two polarization components are detected by corresponding photo detectors which convert the detected light beam to electric signals having several MHz to 100 MHz. The electric signals are amplified if necessary or further beaten down their frequencies to improve measurement sensitivity. Based on the information of amplitude and phase included in the detected polarization components, the polarization state such as the azimuth and ellipticity caused by the DUT can be calculated. Further, based on the azimuth and ellipticity thus obtained, a polarization dependent loss of the DUT can also be calculated.

The ellipsometry optical system of the present invention includes a light source for generating a coherent light beam; a first beam splitter for splitting the coherent light beam into two light beams; an optical frequency shifter for shifting a frequency of one of the two light beams splitted by the first beam splitter to form a reference light beam; a circular polarization converter for circularly polarizing the other of the two light beams splitted by the first beam splitter to form a probing light beam which is a circularly polarized light beam to be applied to the optical device under test; a second beam splitter for combining the reference light beam and the probing light beam that transmitted through the optical device under test; a birefringence prism for receiving a light beam combined by the second beam splitter and separating polarization components which are perpendicular with each other; and a photo detector for receiving the polarization components and converting the same to corresponding electric signals.

In another aspect of the present invention, the optical system is arranged to include a polarization beam splitter whereby a reference light beam is separated into two polarization components perpendicular with each other. Two frequency shifters are provided to frequency shift the two polarization components by the frequencies different from one another. The polarization components are then combined into a reference light beam to be compared with a light beam experienced the birefringence of the DUT.

The combined light beam having beat frequencies includes the information on the polarization state of the light beam passing through the DUT. The combined light beam is detected by the photo detector and converted to an electric signal. The polarization components in the electric signal are separated by band pass filters based on the amount of frequency shifts provided by the frequency shifters. Based on the information of amplitude and phase of the detected polarization components, the polarization state such as the azimuth and ellipticity caused by the DUT can be calculated. Further, based on the azimuth and ellipticity thus obtained, a polarization dependent loss of the DUT can also be calculated.

The ellipsometry optical system of the other aspect of the present invention includes: a light source for generating a coherent light beam; a first beam splitter for splitting the coherent light beam into two light beams; a polarization beam splitter for receiving one light beam of the two light beams splitted by the first beam splitter and for separating the one light beam into two polarization components perpendicular with each other; a first optical frequency shifter for shifting a frequency of one of the polarization components separated by the polarization beam splitter by $\Delta F1$; a second optical frequency shifter for shifting a frequency of the other of the polarization components separated by the polarization beam splitter by $\Delta F2$; means for combining the polarization components which are frequency shifted by the first and second optical frequency shifters to form a reference light beam; a circular polarization converter for circularly polarizing the other of the two light beams splitted by the first beam splitter to form a probing light beam which is a circularly polarized light beam to be applied to the optical device under test; a second beam splitter for combining the reference light beam and the probing light beam that transmitted through said optical device under test; and a photo detector for receiving a light beam combined by the second beam splitter and converting the same to corresponding electric signals.

According to the present invention, the optical system for ellipsometry is capable of analyzing light beams reflected from or transmitted through optical devices under test without including mechanically moving components. Therefore, the optical system of the present invention is able to analyze light beams at high speed.

In one example of the conventional method in which the transmitted light is divided into four light beams and thereby the power levels of each of the light beams is significantly reduced. In the present invention, the optical system for ellipsometry is capable of analyzing light beams reflected from or transmitted through optical devices under test at high detection sensitivity, since the transmitted light is not divided into four light beams.

Further, since the optical system of the present invention analyzes light beams reflected from or transmitted through optical devices under test based on a heterodyne discrimination technology which includes a frequency shifter. Therefore, the optical system of the present invention is able to analyze light beams reflected from or transmitted through optical devices under test at high accuracy and sensitivity by handling relatively low frequency electric signals in a signal analysis process.

Furthermore, the optical system of the present invention separates the polarization components through band pass filters the pass band frequency of which correspond to the frequency shifted by the frequency shifter. Therefore, the optical system of the present invention is able to analyze the light beams reflected from or transmitted through optical devices under test with high resolution since the band pass filters effectively reduces noises occurred in the optical system.

BRIEF DESCRIPTION OF THE DRAWINGS

FIG. 7 shows conventional technologies.

DETAILED DESCRIPTION OF THE PREFERRED EMBODIMENT

Figure 1:
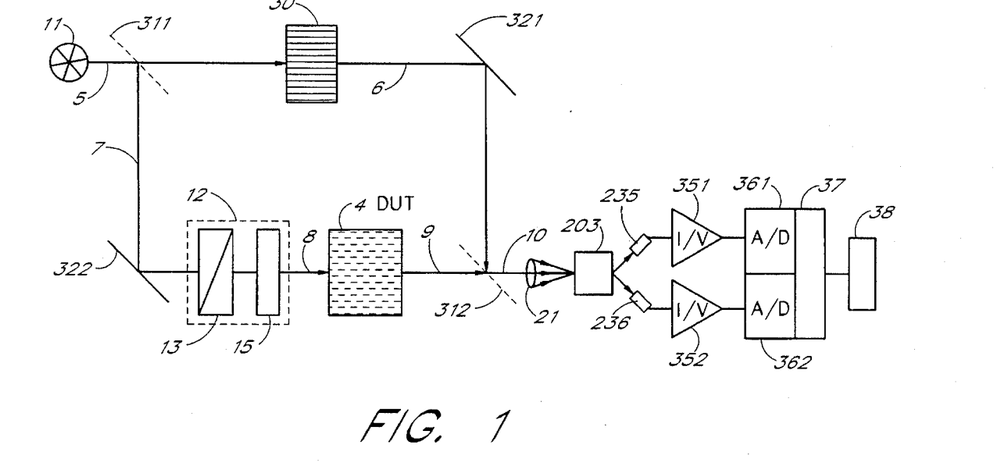
FIG. 1 is a schematic diagram showing a structure of a first embodiment of ellipsometry optical system according to the present invention.

FIG. 1 shows a first embodiment of ellipsometry optical system of the present invention. An optical device DUT 4 under test in FIG. 1 is a transmission type device, such as an optical fiber.

The ellipsometry optical system includes a light source 11, a beam splitter 311, an optical frequency shifter 30, reflectors such as mirrors 321 and 322, a circular polarization converter 12 which is formed of a polarizer 13 and a $\lambda/4$ plate 15, a beam splitter 312, a lens 21, a birefringence prism 203 which is a Wollaston prism in this example, photo detectors 235 and 236, current-voltage converters 351 and 352, A/D converters 361 and 362, an arithmetic unit such as a calculator 37 and a display 38. An optical device under test (DUT) 4 is inserted between the circular polarization converter 12 and the beam splitter 312.

The light source 11 generates a coherent light beam 5 which is for example a linearly polarized light. The light beam 5 is splitted into two light beams by the beam splitter 311. One light beam splitted by the beam splitter 311 is frequency shifted by the optical frequency shifter 30. The optical frequency shifter 30 includes, for example, an acousto-optic effect element to frequency shift the incoming light beam. Such frequency shift is preferably in a range from several MHz to 100 MHz which is a frequency range easily handled by electric circuits.

The frequency shifted light beam 6 can be the linearly polarized light beam as emitted from the light source 11. However, it is preferable to convert the light beam 6 to a circularly polarized light for a convenience of a signal processing in the later stage. Thus, although not shown, a circular polarization convener may be preferably included before or after the frequency shifter 30. The reference light beam 6 is provided to the beam splitter 312 via the mirror 321.

The other light beam splitted by the beam splitter 311 is used as a probing light beam and is provided to the circular polarization converter 12 via the mirror 322. An input light beam is circularly polarized by the circular polarization converter 12. Thus, at the output of the circular polarization converter 12, a circularly polarized light beam 8 is generated which is supplied to the DUT 4.

The light beam 9 transmitted through the DUT 4 is elliptically polarized by the birefringence of the DUT 4 and mixed with the reference light beam 6 at the beam splitter 312. As noted above, although the reference light beam 6 can be a linearly polarized, a circularly polarized light beam is preferable for convenience of the measurement of the polarization state in the light beam 9. For example, when the circularly polarized reference light beam 6 and the elliptically polarized transmitted light beam 9 are superimposed, an optical intensity of each of the polarization components of the superimposed light 10 is subject to the azimuth and ellipticity of the elliptical polarization caused by the DUT 4. The polarization components Ex and Ey which are perpendicular with each other are separated by the birefringence prism 203 typically a Wollaston prism.

Prior to applying to the birefringence prism 203, the superimposed light 10 from the beam splitter 312 is preferably focused by the lens 21. Each of the polarization components Ex and Ey separated by the birefringence prism 203 is converted to an electric current by the photo detectors 235 and 236. The electric currents detected by the photo detectors 235 and 236 in this manner have a beat down frequency which is a difference between the reference light beam 6 and the transmitted light beam 9, i.e., the frequency shifted by the frequency shifter 30.

The electric currents of the polarization components Ex and Ey are converted to electric voltage signals by the current-voltage converters 351 and 352. As noted above, the electric signals have frequencies of several MHz-100 MHz based on the frequency shift by the frequency shifter 30 and have both amplitude information and phase information representing the birefringence of the DUT 4. The electric signals may be further down converted in frequency or amplified in amplitude to be appropriate signals for a signal processing by an electric circuit. The A/D converters 361 and 362 convert the electric signals into corresponding digital data having the amplitude information and phase information. The digital data may preferably be stored in memories in the A/D converters 361 and 362.

The calculator 37 calculates the azimuth and ellipticity of the elliptically polarized beam 9 based on the digital data designating the amplitude Ax, Ay and the relative phase difference δ of the polarization components Ex and Ey. Further, based on the azimuth and ellipticity thus obtained, a polarization dependent loss of the DUT can also be calculated. The result of the calculation may be illustrated by the display 38 or stored in a memory or transmitted to a data bus for further use.

In the foregoing, the Wollaston prism is used as a birefringence prism for separating the incoming light into polarization components perpendicular one another. Other birefringence prism such as a Rochon prism may also be used for this purpose. Further, a Nicol prism or a Glan-Thompson prism may also be used as long as these prisms are able to separately take out the perpendicular polarization components from the light beam transmitted through or reflected from the optical device under test.

In the present invention, it is essential to accurately obtain an amplitude component and a phase component of each polarization component in the light beam. However, since the perpendicular polarization components have different velocity in the birefringence prism, there may be a phase difference between the signals detected by the two photo detectors 235 and 236. Such a phase difference may be eliminated by forming the birefringence prism to have a difference in signal path length for perpendicular polarization components to compensate the phase difference. However, in practice, to make such a prism having the signal path difference is not easy and cost effective.

Therefore, in the preferred embodiment, to compensate the phase difference caused by the birefringence prism, the optical system is calibrated without inserting the DUT 4 prior to the measurement of the DUT. The system measures the composite of the light beam 8 and the reference light beam 6 and memorizes the phase difference between the two polarization components. The phase difference is used to offset the phase data obtained when the DUT is inserted thereby the difference of propagation velocity in the birefringence prism is calibrated.

Figure 2:
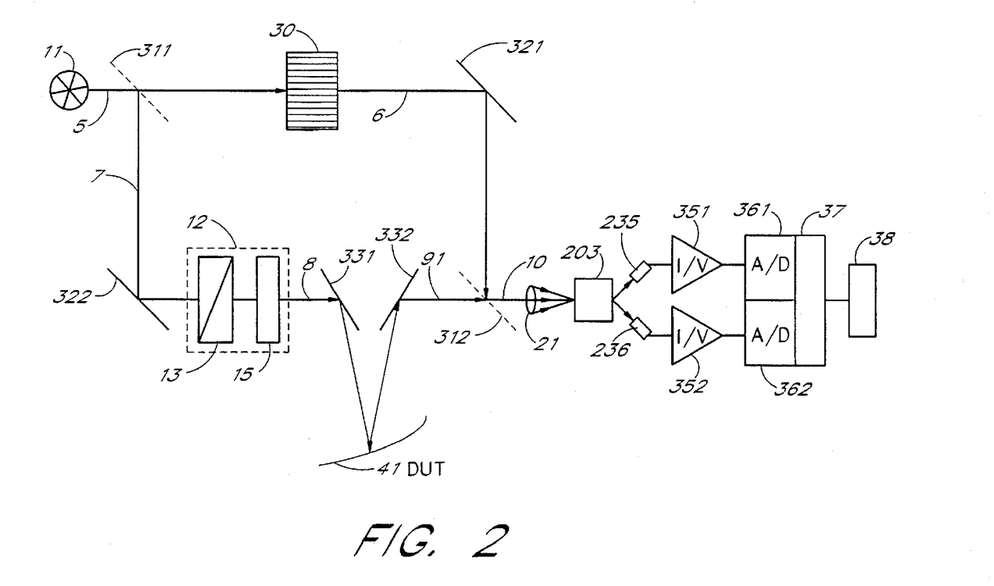
FIG. 2 is a schematic diagram showing a structure of a second embodiment of ellipsometry optical system according to the present invention.

FIG. 2 shows a second embodiment of the present invention. An example of FIG. 2 shows a situation in which an optical device under test (DUT) 41 is a reflection type device where the light beam is reflected from the device under test rather than passing therethrough. An example of such optical device is an optical magnetic memory. In the second embodiment, only the manner of applying the probing light beam to the DUT 41 and receiving the resulting light beam from the DUT 41 is different from the first embodiment of FIG. 1. To do so, the optical system includes reflectors or mirrors 331 and 332. The other parts of the invention are the same as in the invention of FIG. 1.

The probing light beam 8 from the circular polarization converter 12 is changed its direction by the mirror 331 and is irradiated on the DUT 41. The reflected light beam 91 from the DUT 41 is guided by the mirror 332 to be supplied to the beam splitter 312 where it is superimposed with the reference light beam 6. As noted above with reference to FIG. 1, since the reference light beam is frequency shifted by the frequency shifter 30, the superimposed light 10 is a beat light signal the frequency of which is a difference between the reference light beam 6 and the reflected light beam 91.

Although two mirrors 321 and 322 are used to superimpose the reference light beam 6 and the transmitted light beam 9 at the beam splitter 312 in the example of FIG. 1, and two other mirrors 331 and 332 are additionally used to superimpose the reference light beam 6 and the reflected light beam 91 at the beam splitter 312. These are merely examples to explain the embodiment of the present invention, and other arrangement, such as additional mirrors may be equally applicable to the present invention.

As in the foregoing with reference to FIGS. 1 and 2, the ellipsometry optical system of the present invention employs a heterodyne principle to beat down a frequency of a light beam which has been elliptically polarized by transmitting through the DUT. The heterodyne process is undertaken by mixing the light beam passing through the DUT with a reference light which is frequency shifted by several MHz–100 MHz. The composite light signal has a frequency which is equal to the frequency shift and includes information on the polarization state of the light beam passing through the DUT. The composite light beam is provided to a birefringent polarization prism whereby it is divided into two polarization components orthogonal with each other.

These two polarization components are detected by the corresponding photo detectors which convert the detected light beam to electric signals having several MHz to 100 MHz. The electric signals are amplified if necessary or further beat down their frequencies to improve measurement sensitivity. Based on the information of amplitude and phase of the detected polarization components, the polarization state such as the azimuth and ellipticity caused by the DUT can be calculated. Further, based on the azimuth and ellipticity thus obtained, a polarization dependent loss of the DUT can also be calculated.

Figure 3:
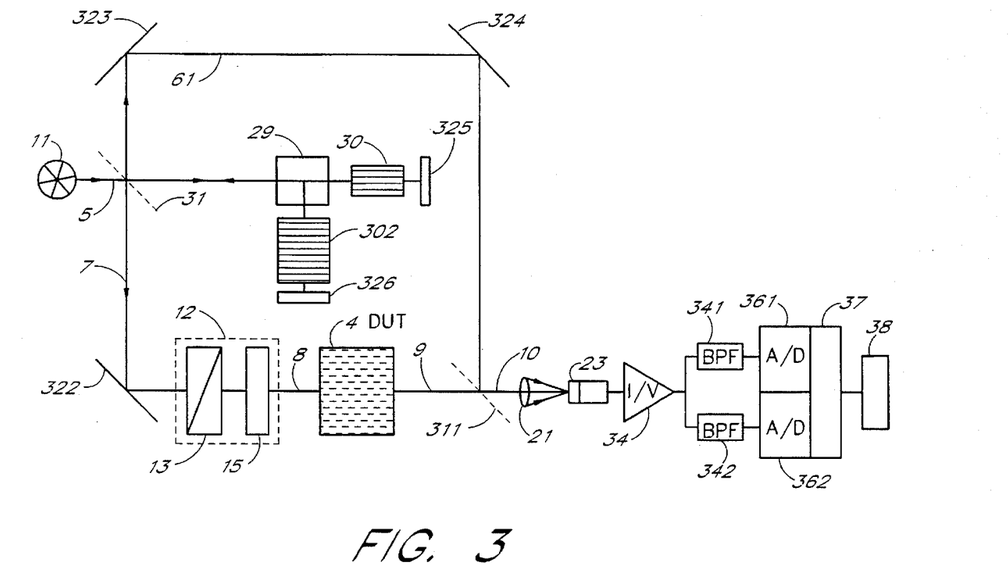
FIG. 3 is a schematic diagram showing a structure of a third embodiment of ellipsometry optical system according to the present invention.

FIG. 3 shows a third embodiment of the present invention. The optical system of FIG. 3 includes a light source 11, a beam splitter 31, a polarization beam splitter 29, optical frequency shifters 301 and 302, mirrors (reflectors) 321–326, a circular polarization converter 12 which is formed of a polarizer 13 and a λ/4 plate 15, a beam splitter 311, a lens 21, a photo detector 23, a current-voltage converter 34, band pass filters 341 and 342, A/D converters 361 and 362, a calculator 37 and a display 38. Further, an optical device under test (DUT) 4 is inserted between the circular polarization converter 12 and the beam splitter 311.

The light source 11 generates a coherent light beam 5 which is for example a linearly polarized light. The light beam 5 is splitted into two light beams by the beam splitter 31. One coherent light beam splitted by the beam splitter 31 travels straight forward and is separated into two polarization components Ex and Ey, which are orthogonal with each other, by the polarization beam splitter 29.

The polarization components Ex ad Ey are respectively frequency shifted by the optical frequency shifters 301 and 302. The optical frequency shifter 30 includes, for example, an acousto-optic effect element to frequency shift the incoming light beam. Such frequency shift is preferably in a range from several MHz to 100 MHz which is a frequency range easily handled by electric circuits.

Thus, for example, the polarization component Ex is frequency shifted by ΔF1 at the optical frequency shifter 301. The ΔF1 shifted light beam is reflected by the mirror 325 and is traveled back to the polarization beam splitter 29. Similarly, the polarization component Ey is frequency shifted by ΔF2 at the optical frequency shifter 302. The ΔF2 shifted light beam is reflected by the mirror 326 and is traveled back to the polarization beam splitter 29. The two light beams are combined by the polarization beam splitter 29 to form a reference light beam 61. The reference light beam 61 is provided to the beam splitter 311 via the beam splitter 31 and the mirrors 323 and 324 as shown in the upper optical path of FIG. 3.

The other light beam splitted by the beam splitter 31 is used as a probing light beam 7 and is provided to the circular polarization converter 12 via the mirror 322 as shown in the lower optical path of FIG. 3. The input light beam is circularly polarized by the polarization converter 12 which is formed of the polarizer 13 and the λ/4 plate 15. Thus, at the output of the circular polarization converter 12, a circularly polarized light beam 8 is generated which is supplied to the DUT 4.

The light beam 9 transmitted through the DUT 4 is elliptically polarized by the birefringence of the DUT 4 and mixed with the reference light beam 61 at the beam splitter 311. As noted above, the reference light beam 61 includes the perpendicular polarization components Ex and Ey which are respectively frequency shifted by ΔF1 and ΔF2 by the frequency shifters 301 and 302.

When the reference light beam 61 and the elliptically polarized transmitted light beam 9 are superimposed, an optical intensity of each of the polarization components Ex and Ey of the superimposed light 10 is subject to the azimuth and ellipticity of the elliptical polarization caused by the DUT 4. In other words, the polarization components Ex and Ey of the composite light 10 include amplitude information and phase information of the elliptical polarization in the transmitted light beam 9 from the DUT 4.

The superimposed light 10 from the beam splitter 312 is preferably focused to a narrow beam by the lens 21 since the light beam emitted from the beam splitter 311 is usually broadened its focus. The light beam focused by the lens 21 is detected by the photo detector 23 which is typically a photo diode. The polarization components Ex and Ey having the frequencies ΔF1 and ΔF2 are converted to electric currents by the photo detectors 23. The electric currents detected by the photo detectors 23 in this manner have beat down frequencies ΔF1 and ΔF2 which are differences between the frequencies of the reference light beam 61 and the transmitted light beam 9, i.e., the frequency shifted by the frequency shifters 301 and 302.

The electric currents of the polarization components Ex and Ey are converted to electric voltage signals by the current-voltage converter 34. As noted above, the electric voltage signals have frequencies (ΔF1 and ΔF2) of several MHz–100 MHz based on the frequency shift by the frequency shifters 301 and 302 and have both the amplitude information and the phase information representing the birefringence of the DUT 4.

The electric signals are separated by the band pass filters 341 ad 342 having their center frequencies corresponding to [delta F1 and delta F2], respectively. As is well known in the art, because the band pass filters 341 and 342 have a narrow frequency pass band, noises such as random noise are reduced at the output of the band pass filters 341 and 342.

The A/D converters 361 and 362 convert the electric signals into corresponding digital data having the amplitude information and phase information. The digital data may preferably be stored in memories in the A/D converters 361 and 362. The calculator 37 calculates the azimuth and ellipticity of the elliptically polarized beam 9 based on the digital data designating the amplitude Ax, Ay and the relative phase difference δ of the polarization components Ex and Ey. Further, based on the azimuth and ellipticity thus obtained, a polarization dependent loss of the DUT can also be calculated. The result of the calculation may be illustrated by the display 38 or stored in a memory or transmitted to a data bus for further use.

Figure 4:
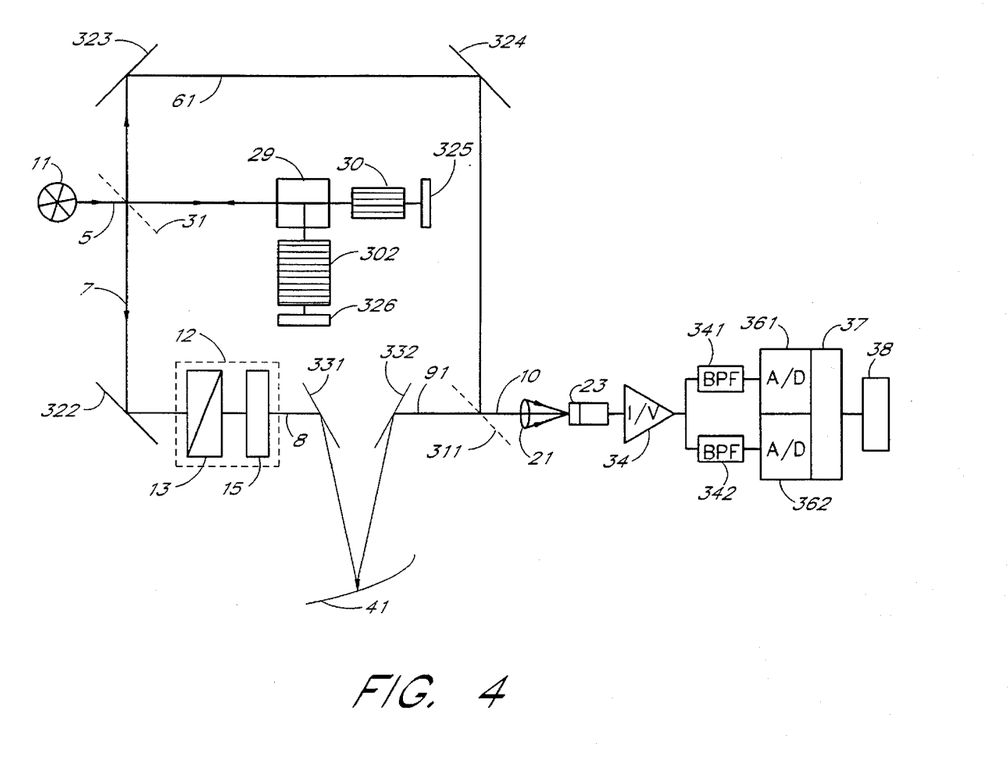
FIG. 4 is a schematic diagram showing a structure of a fourth embodiment of ellipsometry optical system according to the present invention.

FIG. 4 shows a fourth embodiment of the present invention. An example of FIG. 4 shows a situation in which an optical device under test (DUT) 41 is a reflection type device where the light beam is reflected from the device under test rather than passing therethrough. In the fourth embodiment, only the manner of applying the probing light beam to the DUT 41 and receiving the resulting light beam from the DUT 41 is different from the third embodiment of FIG. 3. To do so, the optical system additionally includes mirrors (reflectors) 331 and 332 to guide the light beams. The other parts of the invention are the same as in the invention of FIG. 3.

The probing light beam 8 from the circular polarization converter 12 is changed its direction by the mirror 331 and is irradiated on the DUT 41. The reflected light beam 91 from the DUT 41 is guided by the mirror 332 to be supplied to the beam splitter 311 where it is superimposed by the reference light beam 61. As noted above with reference to FIG. 3, since each of the polarization components of the reference light beam 61 is frequency shifted by ΔF1 and ΔF2 by the frequency shifters 301 and 302, the superimposed light 10 is a light signal having the beat frequencies of which are differences ΔF1 and ΔF2 between the reference light beam 6 and the reflected light beam 91. In the same manner as described with reference to FIG. 3, the polarization components in the combined light are separated by the band pass filters and electrically analyzed to determine the polarization characteristics of the DUT 4.

Figure 5:
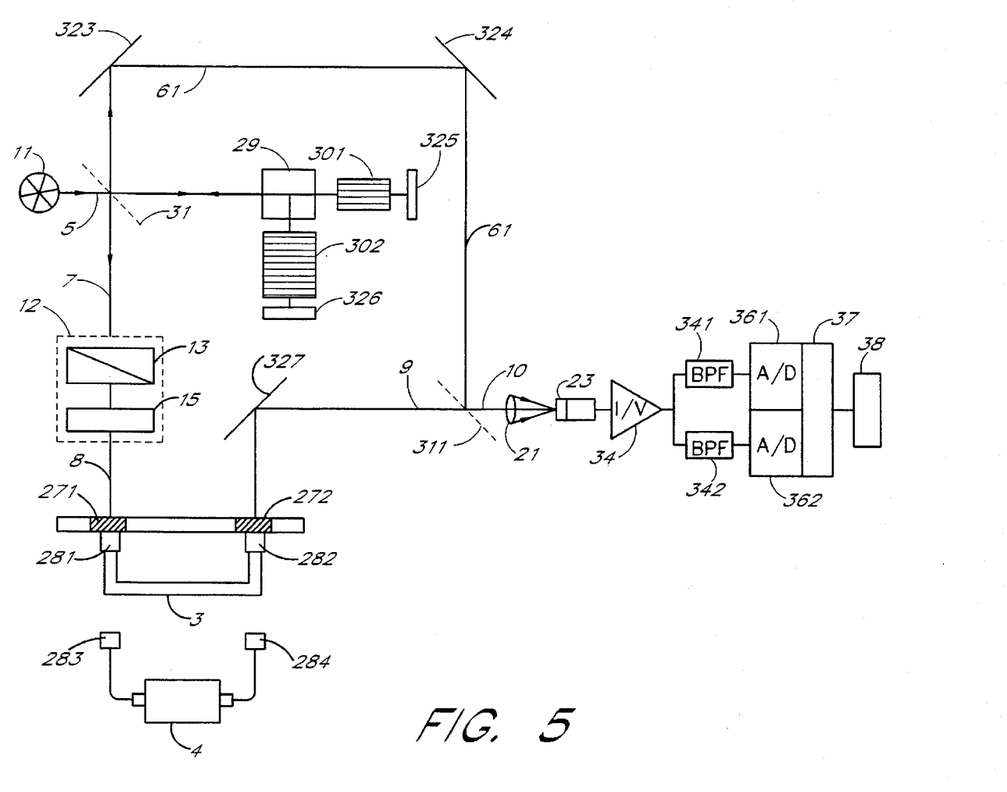
FIG. 5 is a schematic diagram showing a structure of a fifth embodiment of ellipsometry optical system according to the present invention.

FIG. 5 shows a fifth embodiment of the present invention. The basic concept of the invention of FIG. 5 is the same as that of FIGS. 3 and 4. An example of FIG. 5 shows a situation in which an optical device under test (DUT) 4 and a reference optical device 3 are interchangeably connected to the optical system through optical connectors. The measurement results between the DUT 4 and the reference optical device 3 are compared one another to determine the polarization state of the DUT and thus polarization dependent loss of the DUT 4.

In the fifth embodiment, optical connectors 271, 272, 281–284 are provided to receive either the reference optical device 3 or the DUT 4. The light beam 9 transmitted through the reference optical device 3 or the DUT 4 is reflected by a mirror 327 to be guided to the beam splitter 311 where it is combined with the reference light beam 61.

Since each of the polarization components of the reference light beam 61 is frequency shifted by ΔF1 and ΔF2 by the frequency shifters 301 and 302, the superimposed light 10 is a light signal having the beat frequencies of which are differences ΔF1 and ΔF2 between the reference light beam 6 and the reflected light beam 91. In the same manner as described with reference to FIG. 3, the polarization components in the combined light are separated by the band pass filters and electrically analyzed to determine the polarization state of the DUT 4 based on the difference from the polarization state of the reference optical device 3.

As in the foregoing with reference to FIGS. 3–5, the ellipsometry optical system of the present invention employs a heterodyne principle to beat down a frequency of a light beam which has been elliptically polarized by transmitting through the DUT. The heterodyne process is undertaken by separating the reference light beam into two polarization components perpendicular with each other by a polarization beam splitter.

Two frequency shifters are provided to frequency shift the two polarization components by the frequencies different from one another. The polarization components are then combined into a reference light beam. The reference light is superimposed with a light beam that has experienced the birefringence of the DUT thereby the frequency difference is heterodyne detected.

The mixed light beam having beat frequencies includes the information on the polarization state of the light beam passing through the DUT. The combined light beam is detected by the photo detector and converted to an electric signal. The polarization components in the electric signal are separated by band pass filters based on the amount of frequency shift provided by the frequency shifters. Based on the information of amplitude and phase of the detected polarization components, the polarization state such as the azimuth and ellipticity caused by the DUT can be calculated. Further, based on the azimuth and ellipticity thus obtained, a polarization dependent loss of the DUT can also be calculated.

Figure 6:
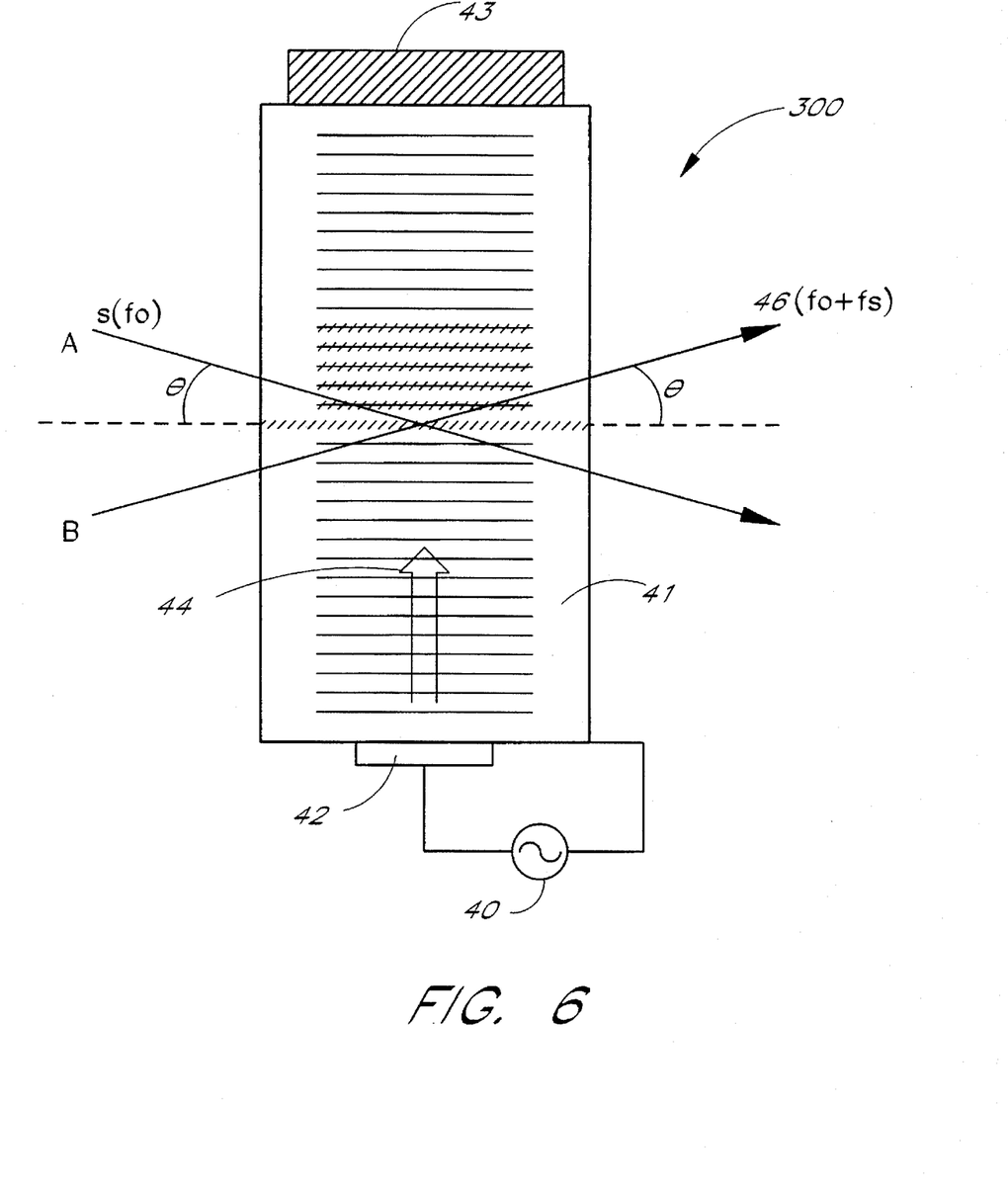
FIG. 6 is a schematic diagram showing an example of optical frequency shifter having an acousto-optic effect element.

FIG. 6 shows an example of an optical frequency shifter to be used in the present invention. The frequency shifters 30, 30 and 302 of the present invention are typically formed of an acousto-optic effect element as shown in FIG. 6. A frequency shifter 300 in FIG. 6 includes a medium base 41 made, for example, of tellurium dioxide (TeO$_2$), a piezoelectric vibrator 42 attached at one end of the medium base 41, an absorber 43 provided at the other end of the medium base 41 and a signal source 40 to drive the piezoelectric vibrator 42.

When the piezoelectric vibrator 42 is driven by the signal source 40, an ultrasonic wave 44 is generated because of the acoustic vibration of the piezoelectric vibrator 42. The ultrasonic wave 44 propagates in the medium base 41 and is absorbed by the absorber 43 at the end of the medium base 41. By the propagation of the ultrasonic wave 44, a compressional wave is formed on the medium base 41 because of the optical elastic effect of refraction factor of the medium base 41. The compressional wave is used as a diffraction grating as described below.

If an incident light 45 is emitted to the medium base 41 in a diagonal direction A as shown in FIG. 6 against the propagation direction of the ultrasonic wave 44, the incident light 45 is diffracted by the diffraction grating function of the medium base 41 to cause a diffracted light 46 in a direction shown in FIG. 6. During this process, the frequency $f_o$ of the incident light 45 is increase by the doppler shift so that the frequency of the diffracted light 46 becomes $[f_o+f_s]$.

The diffracted light 46 is reflected by a mirror as in FIGS. 3–5, the light travels back in an opposite direction of the incident light 45 whereby the frequency is again shifted by $f_s$ by the diffraction. Thus, the light beam coming back from the frequency shifter is frequency shifted by $2f_s$ which is ΔF1 or ΔF2 as described above with reference to FIGS. 3–5.

If an incident light 45 is emitted to the medium base 41 in a diagonal direction B as shown in FIG. 6 which is generally in the same direction of the propagation of the ultrasonic wave 44, the diffracted light 46 is down shifted in the frequency. Thus the frequency of the diffracted light 46 becomes $[f_o-f_s]$ this time. The amount of frequency shift $f_s$ is determined by the angle of incident light and the frequency of the ultrasonic wave 44.

Therefore, by controlling the frequency of the signal source 40 and thus changing the frequency of the ultrasonic wave 44, the optical frequency of the diffracted light 46 can be freely controlled. In other words, by adjusting the frequency of the ultrasonic wave 44, the phase of the reference light beam 6 can be controlled. Further, since the intensity of the diffracted light 46 is dependent on the intensity of the ultrasonic wave 44, it is possible to control the intensity of the diffracted light 46 by adjusting the amplitude of the signal source 40.

As has been described in the foregoing, according to the present invention, the optical system for ellipsometry is capable of analyzing light beams reflected from or transmitted through optical devices under test without including mechanically moving components. Therefore, the optical system of the present invention is able to analyze light beams at high speed.

Unlike one example of the conventional method in which the transmitted light is divided into four light beams, the optical system for ellipsometry is capable of analyzing light beams reflected from or transmitted through optical devices under test at high detection sensitivity, since the transmitted light is not divided into four light beams.

Further, since the optical system of the present invention analyzes light beams reflected from or transmitted through optical devices under test based on a heterodyne discrimination technology which includes a frequency shifter. Therefore, the optical system of the present invention is able to analyze light beams reflected from or transmitted through optical devices under test at high accuracy by handling relatively low frequency electric signals in a signal analysis process.

Furthermore, the optical system of the present invention separates the polarization components through band pass filters the pass band frequency of which correspond to the frequency shifted by the frequency shifter. Therefore, the optical system of the present invention is able to analyze the light beams reflected from or transmitted through optical devices under test with high resolution since the band pass filters effectively reduces noises occurred in the optical system.

What is claimed is:

1. An ellipsometry optical system for analyzing a polarization state of an optical device under test by measuring optical parameters of a light beam which experienced a birefringence of the optical device under test, comprising:

a light source for generating a coherent light beam;

a first beam splitter for splitting said coherent light beam into two light beams;

an optical frequency shifter for shifting a frequency of one of said two light beams splitted by said first beam splitter to form a reference light beam;

a circular polarization converter for circularly polarizing the other of said two light beams splitted by said first beam splitter to form a probing light beam which is a circularly polarized light beam to be applied to the optical device under test;

a second beam splitter for combining said reference light beam and said probing light beam that transmitted through said optical device under test;

a birefringence prism for receiving a light beam combined by said second beam splitter and separating polarization components which are perpendicular with each other; and a photo detector for receiving said polarization components and converting the same to corresponding electric signals.

2. An ellipsometry optical system as defined in claim 1, wherein said optical device under test is a reflection type device whereby said probing light beam reflects back from said optical device under test, said ellipsometry optical system further includes a reflecting plate for guiding said probing light beam reflected from said optical device under test to said second beam splitter.

3. An ellipsometry optical system as defined in claim 1, wherein said reference light beam which is frequency shifted by said frequency shifter is a circularly polarized light beam.

4. An ellipsometry optical system as defined in claim 1, further includes a lens positioned between said second beam splitter and said photo detector to focus a light beam combined by said second beam splitter.

5. An ellipsometry optical system as defined in claim 1, wherein said circular polarization converter includes a polarizer and a ¼ wavelength plate.

6. An ellipsometry optical system as defined in claim 1, wherein said photo detector is formed of a pair of photo diodes each of which receives a corresponding light beam of said polarization components.

7. An ellipsometry optical system as defined in claim 1, wherein said birefringence prism is a type of prism including a Wollaston prism, a Rochon prism, a Nicol prism or a Glan-Thompson prism which is able to deviates polarized plane of an incoming light beam.

8. An ellipsometry optical system as defined in claim 1, wherein said frequency shifter includes an acousto-optic effect element whereby an ultrasonic traveling wave is formed on a base by an external signal source, a doppler frequency shift occurs between frequencies of said ultrasonic wave and an incident light beam.

9. An ellipsometry apparatus for analyzing a polarization state of an optical device under test by measuring optical parameters of a light beam which experienced a birefringence of the optical device under test, comprising:

a light source for generating a coherent light beam;

a first beam splitter for splitting said coherent light beam into two light beams;

an optical frequency shifter for shifting a frequency of one of said two light beams splitted by said first beam splitter to form a reference light beam;

a circular polarization converter for circularly polarizing the other of said two light beams splitted by said first beam splitter to form a probing light beam which is a circularly polarized light beam to be applied to the optical device under test;

a second beam splitter for combining said reference light beam and said probing light beam that transmitted through said optical device under test or reflected back from said optical device under test;

a birefringence prism for receiving a light beam combined by said second beam splitter and separating polarization components which are perpendicular with each other;

a photo detector for receiving said polarization components and converting the same to corresponding electric signals;

an analog-digital converter for converting said electric signals to digital data and storing said digital data in a memory; and an arithmetic unit for receiving said digital data and calculating an azimuth angle and an ellipticity of said light beam that transmitted through or reflected back from said optical device under test.

10. An ellipsometry apparatus as defined in claim 9, wherein said ellipsometry apparatus is calibrated prior to inserting said optical device under test by measuring said light beam combined by said second beam splitter and storing said measured data in said memory, said measured data is used for offsetting data measured when inserting said optical device under test.

11. An ellipsometry apparatus as defined in claim 9, further includes a current-voltage converter connected between said photo detector and said analog-digital converter for converting currents of said electric signals to corresponding voltages.

12. An ellipsometry optical system for analyzing a polarization state of an optical device under test by measuring optical parameters of a light beam which experienced a birefringence of the optical device under test, comprising:

a light source for generating a coherent light beam;

a first beam splitter for splitting said coherent light beam into two light beams;

a polarization beam splitter for receiving one light beam of said two light beams splitted by said first beam splitter and for separating said one light beam into two polarization components perpendicular one another;

a first optical frequency shifter for shifting a frequency of one of said polarization components separated by said polarization beam splitter by $\Delta F1$;

a second optical frequency shifter for shifting a frequency of the other of said polarization components separated by said polarization beam splitter by $\Delta F2$;

means for combining said polarization components which are frequency shifted by said first and second optical frequency shifters to form a reference light beam;

a circular polarization converter for circularly polarizing the other of said two light beams splitted by said first beam splitter to form a probing light beam which is a circularly polarized light beam to be applied to the optical device under test;

a second beam splitter for combining said reference light beam and said probing light beam that transmitted through said optical device under test;

a photo detector for receiving a light beam combined by said second beam splitter and converting the same to corresponding electric signals.

13. An ellipsometry optical system as defined in claim 12, wherein said optical device under test is a reflection type device whereby said probing light beam reflects back from said optical device under test, said ellipsometry optical system further includes a reflecting plate for guiding said probing light beam reflected from said optical device under test to said second beam splitter.

14. An ellipsometry optical system as defined in claim 12, further includes a first reflector for totally reflecting a light beam from said first optical frequency shifter and a second reflector for totally reflecting a light beam from said second optical frequency shifter.

15. An ellipsometry optical system as defined in claim 12, further includes a lens positioned between said second beam splitter and said photo detector to focus a light beam combined by said second beam splitter.

16. An ellipsometry optical system as defined in claim 12, wherein said circular polarization converter includes a polarizer and a ¼ wavelength plate.

17. An ellipsometry optical system as defined in claim 12, wherein said photo detector is formed of a pair of photo diodes each of which receives a corresponding light beam of said polarization components.

18. An ellipsometry optical system as defined in claim 12, wherein said frequency shifter includes an acousto-optic effect element whereby an ultrasonic traveling wave is formed on a base by an external signal source, a doppler frequency shift occurs between frequencies of said ultrasonic wave and an incident light beam.

19. An ellipsometry apparatus for analyzing a polarization state of an optical device under test by measuring optical parameters of a light beam which experienced a birefringence of the optical device under test, comprising:

a light source for generating a coherent light beam;

a first beam splitter for splitting said coherent light beam into two light beams;

a polarization beam splitter for receiving one light beam of said two light beams splitted by said first beam splitter and for separating said one light beam into two polarization components perpendicular one another;

a first optical frequency shifter for shifting a frequency of one of said polarization components separated by said polarization beam splitter by $\Delta F1$;

a second optical frequency shifter for shifting a frequency of the other of said polarization components separated by said polarization beam splitter by $\Delta F2$;

means for combining said polarization components which are frequency shifted by said first and second optical frequency shifters to form a reference light beam;

a circular polarization converter for circularly polarizing the other of said two light beams splitted by said first beam splitter to form a probing light beam which is a circularly polarized light beam to be applied to the optical device under test;

a second beam splitter for combining said reference light beam and said probing light beam that transmitted through said optical device under test;

a photo detector for receiving a light beam combined by said second beam splitter and converting the same to corresponding electric signals;

an analog-digital converter for converting said electric signals to digital data and storing said digital data in a memory; and an arithmetic unit for receiving said digital data and calculating an azimuth angle and an ellipticity of said light beam that transmitted through or reflected back from said optical device under test.

20. An ellipsometry apparatus as defined in claim 19, further includes a current-voltage converter connected between said photo detector and said analog-digital converter for converting currents of said electric signals to corresponding voltages.

21. An ellipsometry apparatus as defined in claim 19, wherein said optical device under test and a reference optical device are interchangeably connected to said ellipsometry apparatus for obtaining a polarization dependent loss of said optical device under test by comparing measured data of said reference optical device and said optical device under test.

* * * * *